(12) United States Patent
Prentakis et al.

(10) Patent No.: US 10,912,624 B2
(45) Date of Patent: Feb. 9, 2021

(54) SYSTEM AND APPARATUS FOR SENSING CONTACT ON A ROBOTIC MECHANISM IN A CATHETER PROCEDURE SYSTEM

(71) Applicant: Corindus, Inc., Waltham, MA (US)

(72) Inventors: Antonios E. Prentakis, Watertown, MA (US); Robert Elden, Cambridge, MA (US); Nicholas Kottenstette, Worcester, MA (US); Franklin Eventoff, Skagit, WA (US)

(73) Assignee: Corindus, Inc., Waltham, MA (US)

( * ) Notice: Subject to any disclaimer, the term of this patent is extended or adjusted under 35 U.S.C. 154(b) by 473 days.

(21) Appl. No.: 15/701,009

(22) Filed: Sep. 11, 2017

(65) Prior Publication Data

US 2019/0076208 A1    Mar. 14, 2019

(51) Int. Cl.
| | |
|---|---|
| *A61B 90/00* | (2016.01) |
| *A61M 25/01* | (2006.01) |
| *A61B 34/20* | (2016.01) |
| *A61B 34/37* | (2016.01) |
| *A61B 34/30* | (2016.01) |

(52) U.S. Cl.
CPC ............. *A61B 90/06* (2016.02); *A61B 34/20* (2016.02); *A61B 34/37* (2016.02); *A61M 25/0113* (2013.01); *A61M 25/0116* (2013.01); *A61B 2034/301* (2016.02); *A61B 2090/065* (2016.02); *A61M 2025/0166* (2013.01)

(58) Field of Classification Search
CPC ........ A61B 2034/301; A61B 2090/065; A61B 34/20; A61B 34/37; A61B 90/06; A61M 2025/0166; A61M 25/0113; A61M 25/0116
See application file for complete search history.

(56) References Cited

U.S. PATENT DOCUMENTS

2012/0179167 A1* 7/2012 Wenderow ............. A61B 34/30
                                                                   606/130

* cited by examiner

*Primary Examiner* — Brandy S Lee

(57) ABSTRACT

A contact sensor assembly includes a sensor comprising a plurality of sensing areas, a plurality of non-sensing areas, and a connector coupled to the plurality of sensing areas. The contact sensor assembly also include an outer cover positioned over the sensor. The outer cover has an inner surface and an outer surface. The inner surface includes a plurality of raised portions and at least one corner section. The at least one corner section of the inner surface of the outer cover is reinforced so that the corner section has a greater stiffness and the corner section corresponds to at least one non-sensing area of the sensor.

8 Claims, 18 Drawing Sheets

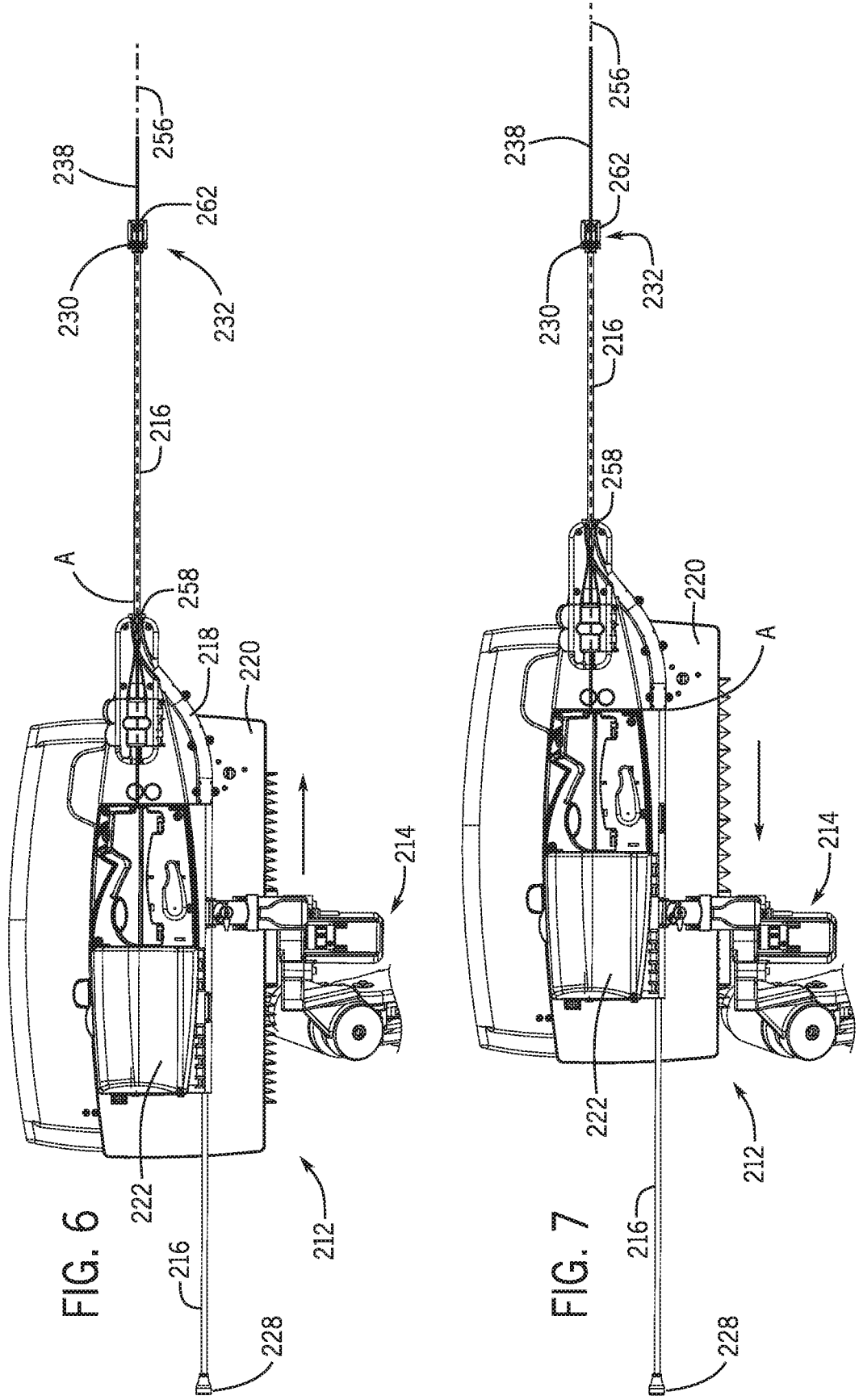

SYSTEM AND APPARATUS FOR SENSING CONTACT ON A ROBOTIC MECHANISM IN A CATHETER PROCEDURE SYSTEM

FIELD OF THE INVENTION

The present invention relates generally to the field of robotic catheter systems for performing diagnostic and/or therapeutic procedures and in particular, to a system and apparatus for sensing contact on a robotic mechanism in a catheter procedure system.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then guided to the desired location, most commonly in one of the heart vessels or elsewhere in the vascular system. At this point, the catheter is slid over the guide wire into the blood vessel and/or heart. In some procedures, the catheter is equipped with a balloon or stent that when deployed at the site of the lesion allows for increased blood flow through the portion of the coronary artery that is affected by the lesion.

For manual insertion of a catheter, the physician applies torque and axial push force on the proximal end of a guide wire to effect tip direction and axial advancement at the distal end. Robotic catheter systems have been developed that may be used to aid a physician in performing a catheterization procedure such as a percutaneous coronary intervention (PCI). The physician uses a robotic catheter system to precisely steer a coronary guide wire, balloon catheter or stent delivery system in order to, for example, widen an obstructed artery. In order to perform PCI, the various elongated medical devices (e.g., guide wire, guide catheter, working catheter) must be navigated through the coronary anatomy to a target lesion. While observing the coronary anatomy using fluoroscopy, the physician manipulates the elongated medical device into the appropriate vessels toward the lesion and avoids advancing into side branches. A robotic catheter procedure system includes drive mechanisms to drive various elongated medical devices (e.g., guide wire, guide catheter, working catheter) used in catheterization procedures to provide linear and rotational movement of the elongated medical device.

During a catheter procedure, the various element of the robotic catheter system may be moved linearly toward the patient. It would be desirable to provide a sensing system and apparatus that detects when contact is made with the elements of the robotic catheter system. The linear movement of the elements of the robotic catheter system may be halted in response to the detection of the contact (e.g., with the patient).

BRIEF DESCRIPTION OF THE INVENTION

In accordance with an embodiment, a contact sensor assembly includes a sensor comprising a plurality of sensing areas, a plurality of non-sensing areas and a connector coupled to the plurality of sensing areas and an outer cover positioned over the sensor, the outer cover having an inner surface and an outer surface, the inner surface comprising a plurality of raised portions and at least one corner section; the at least one corner section is reinforced so that the corner section has a greater stiffness and the corner section corresponds to at least one non-sensing area of the sensor.

In accordance with another embodiment, a contact sensor assembly includes a sensor comprising a plurality of sensing areas, a plurality of non-sensing areas and a connector coupled to the plurality of sensing areas, the sensor configured to be attached to a surface having a plurality of flat sections, wherein each sensing area corresponds to a flat section and each non-sensing area corresponds to a location where the sensor is bent so that each sensing area conforms to a flat section of the surface; and an outer cover positioned over the sensor, the outer cover having an inner surface and an outer surface, the inner surface comprising a plurality of raised portions.

In accordance with another embodiment, a catheter procedure system includes a bedside system comprising at least one percutaneous device and at least one drive mechanism coupled to the at least one percutaneous device, the drive mechanism comprising a housing having a distal end and a contact sensor assembly positioned on the distal end of the housing; the contact sensor assembly includes a sensor comprising a plurality of sensing areas, a plurality of non-sensing areas and a connector coupled to the plurality of sensing areas and an outer cover positioned over the sensor, the outer cover having an inner surface and an outer surface, the inner surface comprising a plurality of raised portions and the catheter procedure system further includes a processor coupled to the contact sensor assembly and a workstation coupled to the bedside system; the workstation includes a user interface, at least one display, and a controller coupled to the bedside system, the user interface, the at least one display and the processor coupled to the contact sensor assembly.

BRIEF DESCRIPTION OF THE DRAWINGS

The invention will become more fully understood from the following detailed description, taken in conjunction with the accompanying drawings, wherein the reference numerals refer to like parts in which:

FIG. 6 is a top plan view of the catheter procedure system with the robotic mechanism in a first position in accordance with an embodiment;

FIG. 7 is a top plan view of the catheter procedure system with the robotic mechanism in a second extended position in accordance with an embodiment;

DETAILED DESCRIPTION

Figure 1:
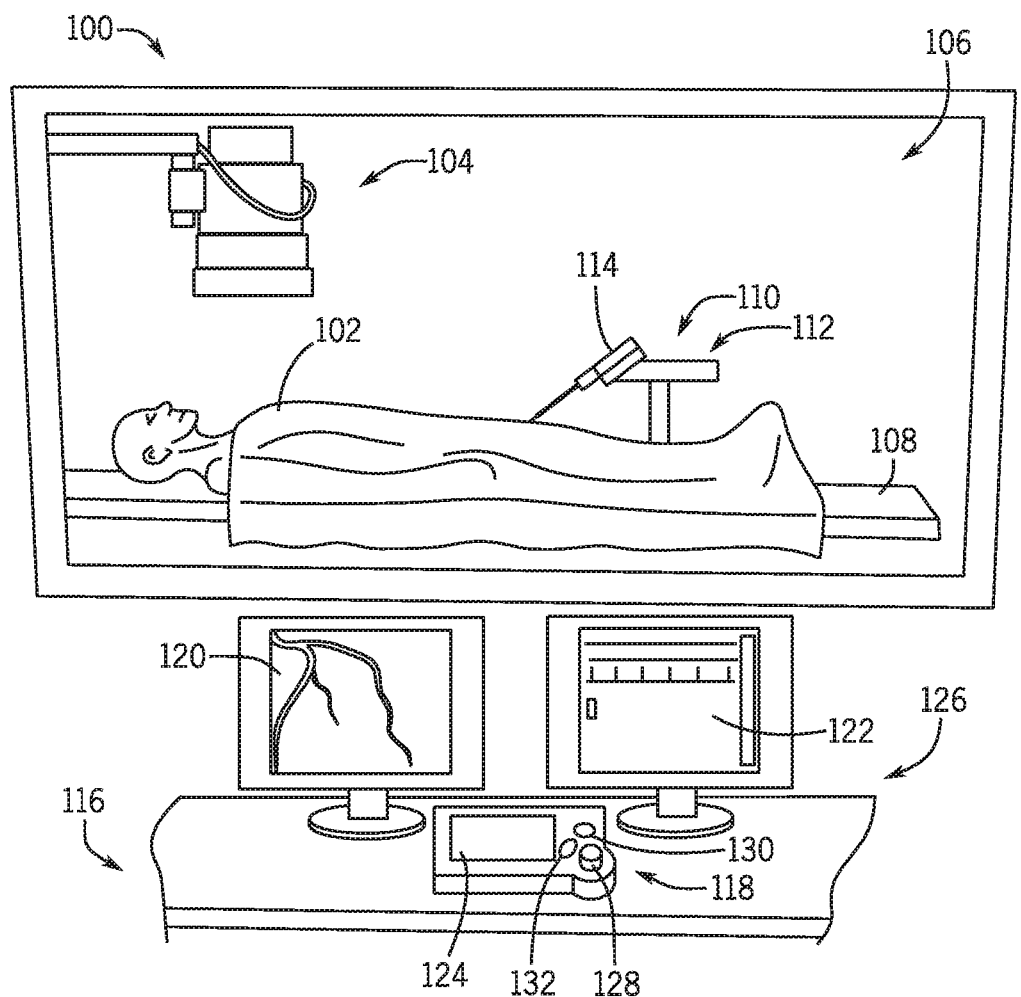
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the diagnosis and/or treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery systems, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 114 (e.g., a cassette) supported by a robotic arm 112 which is used to automatically feed a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 2) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 114 includes various drive mechanisms to cause movement (e.g., axial and rotational movement) of the components of the bedside system 110 including the percutaneous intervention devices.

In one embodiment, controls 118 include a touch screen 124, one or more joysticks 128 and buttons 130, 132. The joystick 128 may be configured to advance, retract, or rotate various components and percutaneous intervention devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 2) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

Figure 2:
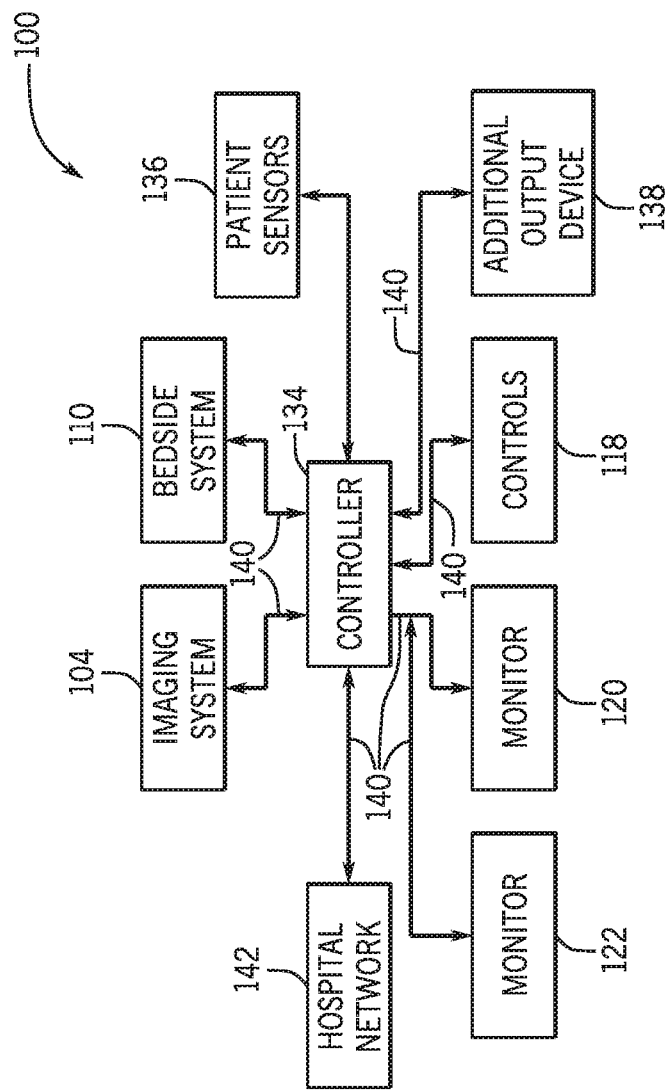
FIG. 2 a schematic block diagram of a catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include image processing engines, data storage and archive systems, automatic balloon and/or stent inflation systems, medicine injection systems, medicine tracking and/or logging systems, user logs, encryption systems, systems to restrict access or use of catheter procedure system 100, etc.

As mentioned, controller 134 is in communication with bedside system 110 and may provide control signals to the bedside system 110 to control the operation of the motors and drive mechanisms used to drive the percutaneous intervention devices (e.g., guide wire, catheter, etc.). The bedside system 110 may include, for example, a guide wire axial drive mechanism that provides for advancement and/or retraction of a guide wire, a working catheter axial drive mechanism that provides for advancement and/or retraction of a working catheter and a guide wire rotational drive mechanism that is configured to cause a guide wire to rotate about its longitudinal axis. In one embodiment, the various drive mechanism are housed in a drive assembly 114 (shown in FIG. 1).

Figure 3:
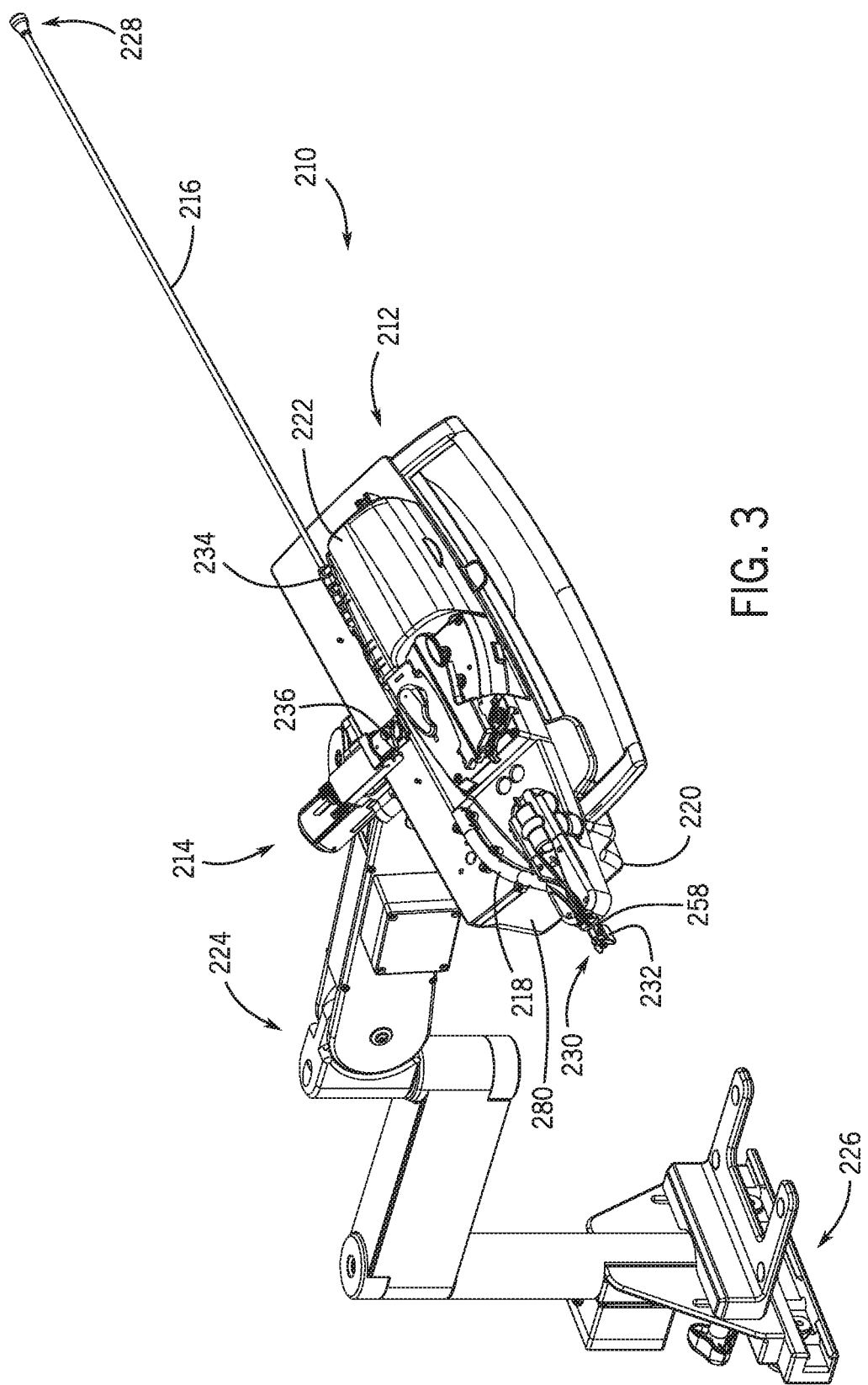
FIG. 3 is an isometric view of a bedside system of a catheter procedure system in accordance with an embodiment.

FIG. 3 is an isometric view of a bedside system of a catheter procedure system in accordance with an embodiment. In FIG. 3, a bedside system 210 includes a robotic mechanism 212 that may be used to robotically move an elongated medical device. The robotic mechanism 212 is movable relative to a base 214. The robotic mechanism 212 includes a robotic drive base 220 movable relative to base 214 and a drive assembly 222 that is operatively secured to robotic drive base 220. In FIG. 3, the drive assembly 222 is shown as a cassette that houses the various drive mechanisms used to drive the percutaneous devices and that may be equipped with the percutaneous devices. In one embodiment, base 214 is secured to an articulating arm 224 that allows a user to position robotic mechanism 212 proximate a patient. In an embodiment, base 214 is the distal portion of the articulating arm 224. Articulating arm 224 is secured to a patient bed by a rail clamp or a bed clamp 226. By manipulation of articulated arm 224, the base 214 is placed in a fixed location relative to a patient that lies upon the patient bed. The joints of the articulated arm can be locked once the desired location of robotic mechanism 212 is set relative to the patient.

As used herein, the direction distal is the direction toward the patient and the direction proximal is the direction away from the patient. The term up and upper refers to the general direction away from the direction of gravity and the term bottom, lower and down refers to the general direction of gravity. The term front refers to the side of the robotic mechanism that faces a user and away from the articulating arm. The term rear refers to the side of the robotic mechanism that is closest to the articulating arm. The term inwardly refers to the inner portion of a feature. The term outwardly refers to the outward portion of a feature.

Bedside system 210 also includes a flexible track 216 that is movable along a rigid guide track 218 having a non-linear portion. The flexible track 216 includes a proximal end 228 and a distal end 230. The flexible track 216 supports an elongated medical device such as a guide catheter so that the guide catheter can be advanced into the patient without buckling. In one embodiment, drive assembly 222 includes structure that defines rigid guide 218. In another embodiment, base 214 alone or in combination with drive assembly 222 includes structure that defines rigid guide 218.

The flexible tack 216 is initially positioned within the rigid guide 218 by feeding distal end 230 of flexible track 216 into proximal opening 234 of rigid guide 218 until the distal end 230 of flexible track 216 extends beyond collar 258 of rigid guide 218. The distal end 230 of flexible track 216 is operatively connected to the sheath clip 232. The rigid guide includes a linear portion beginning at proximal opening 234 and a non-linear portion. In one embodiment, the non-linear portion is an arcuate portion having at least one point of inflection.

Figure 4:
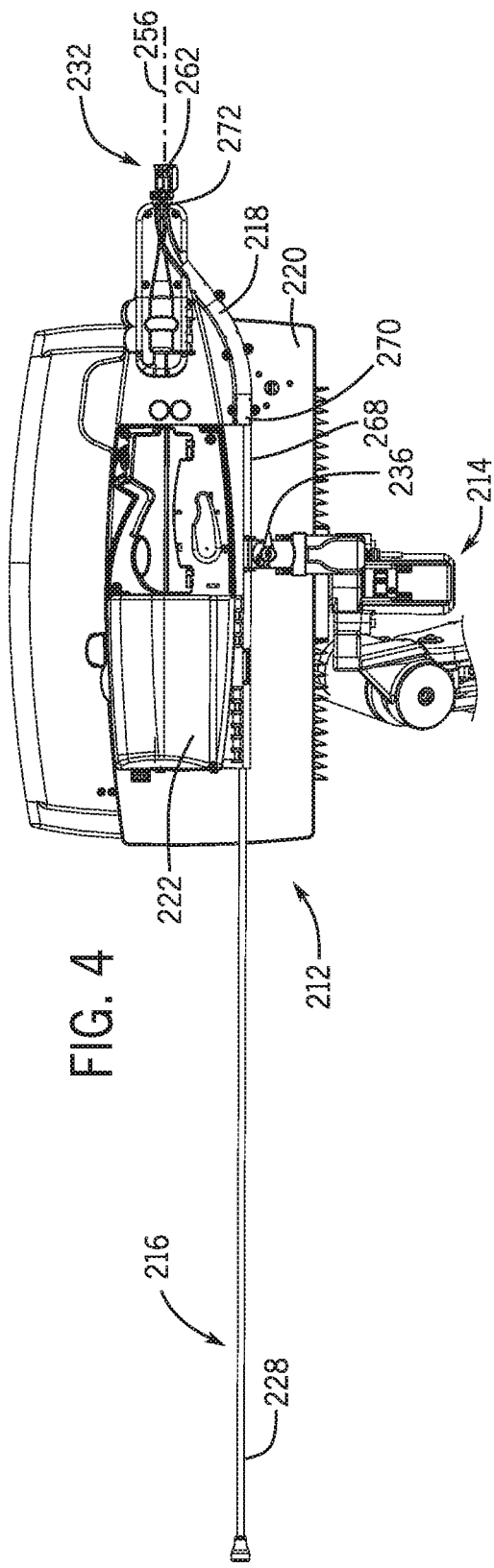
FIG. 4 is a top plan view of the catheter procedure system with the flexible track in the fully retracted position in accordance with an embodiment.
Figure 5:
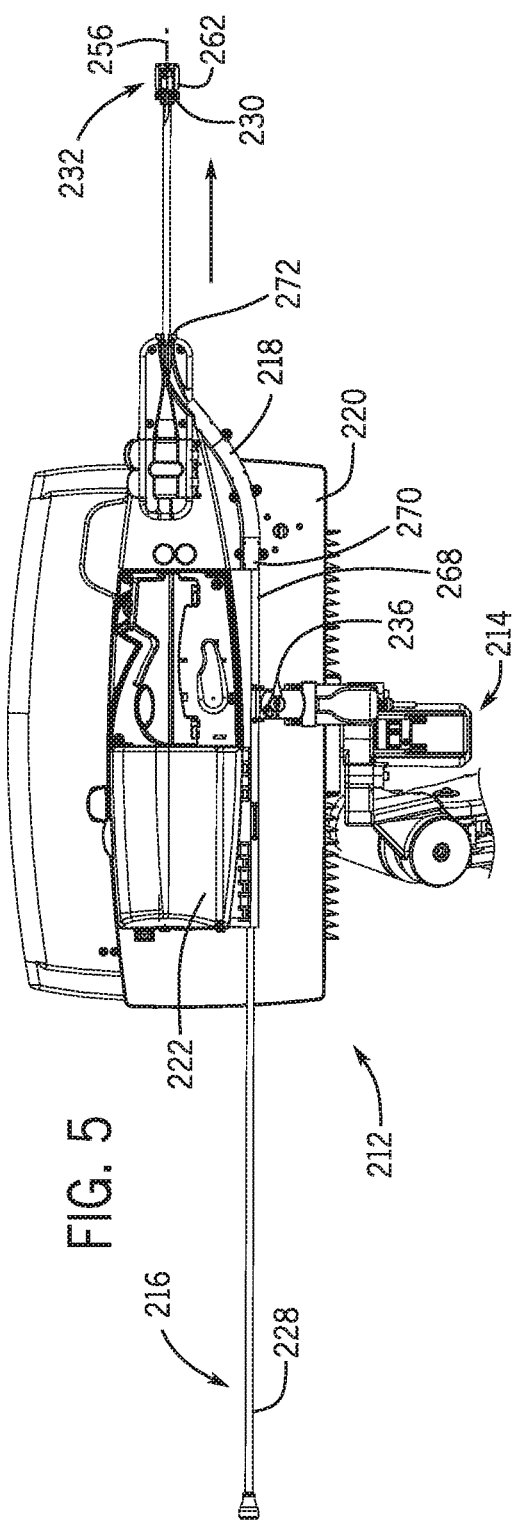
FIG. 5 is a top plan view of the catheter procedure system with the flexible track in an extended position in accordance with an embodiment.

Referring to FIGS. 4 and 5, to perform a procedure the sheath clip 232 is pulled by a user away from drive assembly 222 in a direction along longitudinal axis 256 until the distal end 262 of sheath clip 232 is proximate the patient. In one embodiment, an introducer (not shown) is secured to the distal end 262 of sheath clip 232. The introducer is a device that is secured to a patient to positively position the introducer to the patient to allow insertion and removal of elongated medical devices such as a guide catheter, guide wire and/or working catheter into the patient with minimal tissue damage to the patient. Once the operator has pulled the sheath clip 232 and accompanying flexible track 216 toward the patient such that the introducer is proximate the patient, the flexible track 216 is locked in position by a locking clamp 236. The locking clamp 236 secures the flexible track 216 to base 214 such that a portion of flexible track 216 is in a fixed position relative to the patient bed and the patient to the extent the patient lies still on the patient bed.

Figure 8:
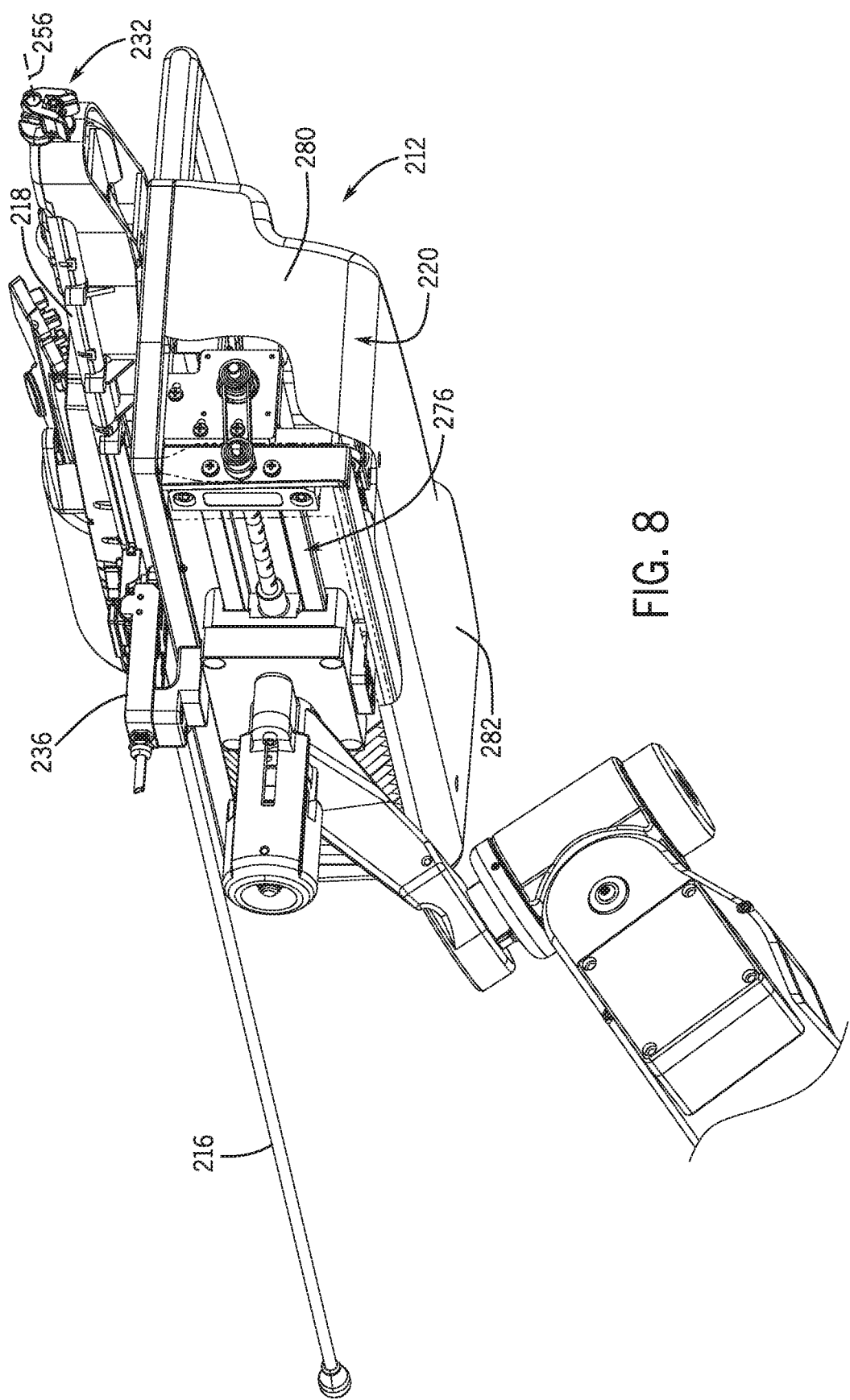
FIG. 8 is a rear isometric view of the catheter procedure system with a linear drive in accordance with an embodiment.

Referring to FIG. 8, robotic mechanism 212 includes a linear drive mechanism 276 that is disposed within a housing 282 of the robotic drive base 220. The linear drive mechanism 276 shown in FIG. 8 includes a linear slide that is robotically controlled by a user through a remote workstation (for example, workstation 116 shown in FIG. 1). The linear drive mechanism 276 drives robotic mechanism 212 along longitudinal axis 256. Since rigid guide 218 is fixed relative to robotic mechanism 212, the rigid guide 218 and robotic mechanism 212 move relative to the flexible track 216 as the robotic mechanism 212 moves along the longitudinal axis 256.

Referring to FIG. 4 and FIG. 5, the operation and movement of flexible track 216 relative to rigid guide 218 will be described. Referring to FIG. 4, flexible track 216 is shown in the installation first position in which guide catheter 238 (shown in FIGS. 6 and 7) is positioned within sheath clip 232 and flexible track opening (not shown) as described above. Referring to FIG. 5, once sheath clip 232 has been released from the drive assembly 222, the sheath clip 232 and distal end 230 of the flexible track 216 are pulled by a user away from drive assembly 222 such that the distal end 262 of the sheath clip 232 is proximate the entry point of the patient in which a percutaneous intervention will occur. The locking clamp 236 operatively clamps a portion of flexible track 216 so that flexible track 216 is fixed relative to base 214.

Referring to FIGS. 4 and 5, the portion of flexible track 216 that is positioned within the arcuate portion of rigid guide 218 is pulled out of the distal end 262 of rigid guide 218 in a direction generally along longitudinal axis 256. Similarly, a portion 268 of flexible track 216 that was external to and not located within the arcuate portion of rigid guide 218 is pulled into the arcuate portion of rigid guide 218 and depending on how far the terminal distal end 230 of the flexible track 216 is pulled toward the patient, portion 268 of flexible track 216 will enter the arcuate portion of rigid guide and may extend therefrom. Stated another way, flexible track 216 includes three general regions that change with the operation of the guide catheter system. First, a proximal region that includes the flexible track portion from the proximal end 228 of flexible track 216 to the proximal end 270 of the arcuate portion of rigid guide 218. Flexible track 216 includes a second portion located between the proximal end 270 of the arcuate portion of rigid guide 218 and the distal end 272 of the arcuate portion of rigid guide 218 proximate collar 258. Flexible track 216 includes a third region that extends from collar 258 of rigid guide 218 in a direction defined by a vector generally along longitudinal axis 256, where the vector has a beginning at the Y-connector and extends in a direction toward collar 258. The first region and second region of flexible track 216 as described above is offset from and not in line with longitudinal axis 256. The third portion of flexible track 216 is generally coaxial with longitudinal axis 256 as flexible track 216 exits collar 258 of rigid guide 218.

During one type of intervention procedure, guide catheter 238 (shown in FIGS. 6 and 7) is inserted into a patient's femoral artery through an introducer and positioned proximate the coronary ostium of a patient's heart. An operator may wish to relocate the distal end of the guide catheter robotically. Referring to FIGS. 6 and 7, the control of the distal end of guide catheter 238 and the movement of the robotic mechanism 212 and rigid guides 218 relative to the flexible track 216 will be described. Referring to FIG. 6, guide catheter 238 has a distal portion which extends beyond the distal end 262 of sheath clip 232 in order to extend the terminal end of guide catheter 238 in a direction away from the terminal distal end 262 of the sheath clip 232. As noted above, the distal end of guide catheter 238 may be placed proximate the ostium of a patient. The robotic control of the distal end of the guide catheter 238 is accomplished by movement of robotic drive mechanism 212 relative to base 214 and flexible track 216 by linear drive 276 (shown in FIG. 8). The guide catheter 238 is located within the channel of the flexible track 216 from drive assembly 222 until the sheath clip 232.

If during a PCI procedure the guide catheter begins to slip out of the ostium, it is possible to extend the distal end of guide catheter 238 back into the patient ostium by robotically moving the robotic mechanism 212 towards the patient. In doing so, the distal end of guide catheter 238 is moved toward the patient reinserting or seating the distal end of the guide catheter into the patient's ostium as one example. As the robotic drive mechanism 212 is moved along longitudinal axis 256, the rigid guide 218 is moved relative to the flexible track 216. The portion of flexible track 216 that is located within the arcuate section of rigid guide 218 changes as the robotic mechanism 212 and rigid guide 218 are moved. The portion of the flexible track 216 that is located in the rigid guide is moved toward and away from longitudinal axis 256 depending on the direction that the robotic drive mechanism 212 is moving. Guide catheter 238 moves into or out of the section of flexible track 216 that is moving in and out of the arcuate portion of rigid guide 218. In this manner, the portion of guide catheter 238 between drive assembly 222 and the sheath clip 232 is always located within the channel of flexible track 216. In this manner, guide catheter 238 may be manipulated within flexible track 216 without buckling or causing other non-desirable movement during a percutaneous intervention procedure.

Referring to FIGS. 6 and 7, the position of the flexible track 216 with respect to rigid guide 218 will be described as it related to a single section A on flexible track 216. In one example, section A on flexible track 216 is located distal collar 258 of rigid guide 218. When an operator determines to insert guide catheter 238 further into or toward a patient in a direction away from collar 258, an input device is manipulated by the user at a remote workstation that drives robotic drive 212 distally along longitudinal axis 256 by activating linear drive 276. The proximal end of guide catheter 238 is longitudinally fixed in drive assembly 222 so that as the robotic drive 212 including drive assembly 222 is moved relative to base 214 and flexible track 216 by linear drive 276 (shown in FIG. 8) in a direction toward the patient, the guide catheter 238 moves distally along longitudinal axis 256. As a result, the distal end of guide catheter 238 moves toward and/or into the patient.

As the robotic mechanism 212 is moved along longitudinal axis 256, section A of flexible track 216 moves into the arcuate portion of rigid guide 218 through collar 258 and along the arcuate portion of rigid guide until section A of the flexible track 216 is adjacent the proximal end of rigid guide 218. In this manner, distal end 230 of flexible track 216 remains in a constant position but section A of flexible track 216 is moved out of or offset to the longitudinal axis 256. As section A moves into the arcuate channel defined by the rigid guide 218, the guide catheter 238 enters the channel or hollow lumen of the flexible track 216 through the slit adjacent in the engagement zone proximal to collar 258. In this manner, flexible track 216 provides continual support and guidance for the guide catheter 238 between the collar 258 and the patient as the distal end of guide catheter 238 is moved toward and away from the patient.

Similarly, if the operator desires to retract the distal end of the guide catheter 238 from within the patient, the user provides a command to the linear drive 276 through the remote workstation to move robotic drive mechanism 212 in a direction away from the patient. In this way, section A of the flexible track 216 would enter the proximal end of the arcuate portion of the rigid guide and be guided within the channel of the rigid guide 218 until section A exits the distal end of the rigid guide 218. The guide catheter 238 would enter the slit at section A or stated another way, a portion of the guide catheter 238 would enter the flexible track 216 via the portion of the slit that is located within the concentric circle taken at section A of the flexible track 216. Note that although sections of the flexible track are positioned in different regions of the rigid guide as the robotic mechanism is moved toward and away from the patient the proximal end and the distal end of the flexible track remain in a fixed location as the robotic mechanism is moved along the longitudinal axis.

As the robotic drive mechanism 212 is moved in a direction towards the patient, the distal end 280 (shown in FIGS. 3 and 8) of the robotic drive base 220 may make contact with objects or obstacles such as the patient. The distal end 280 of the robotic drive base 220 may include a contact sensor assembly (e.g., a bumper sensor assembly) to detect contact with an object. As discussed further below, movement of the robotic drive mechanism 212 may be stopped if contact is detected by the contact sensor assembly.

Figure 9:
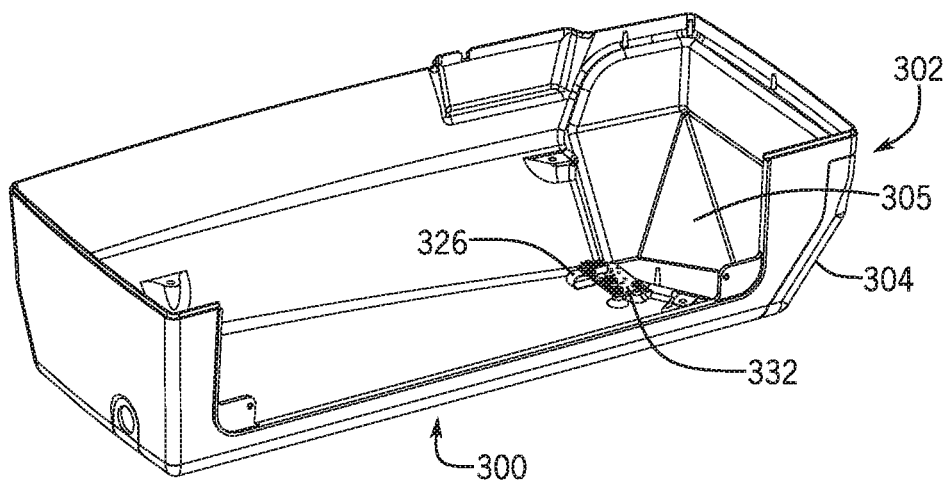
FIG. 9 is a perspective view of a bottom portion of a robotic mechanism housing in accordance with an embodiment.
Figure 10:
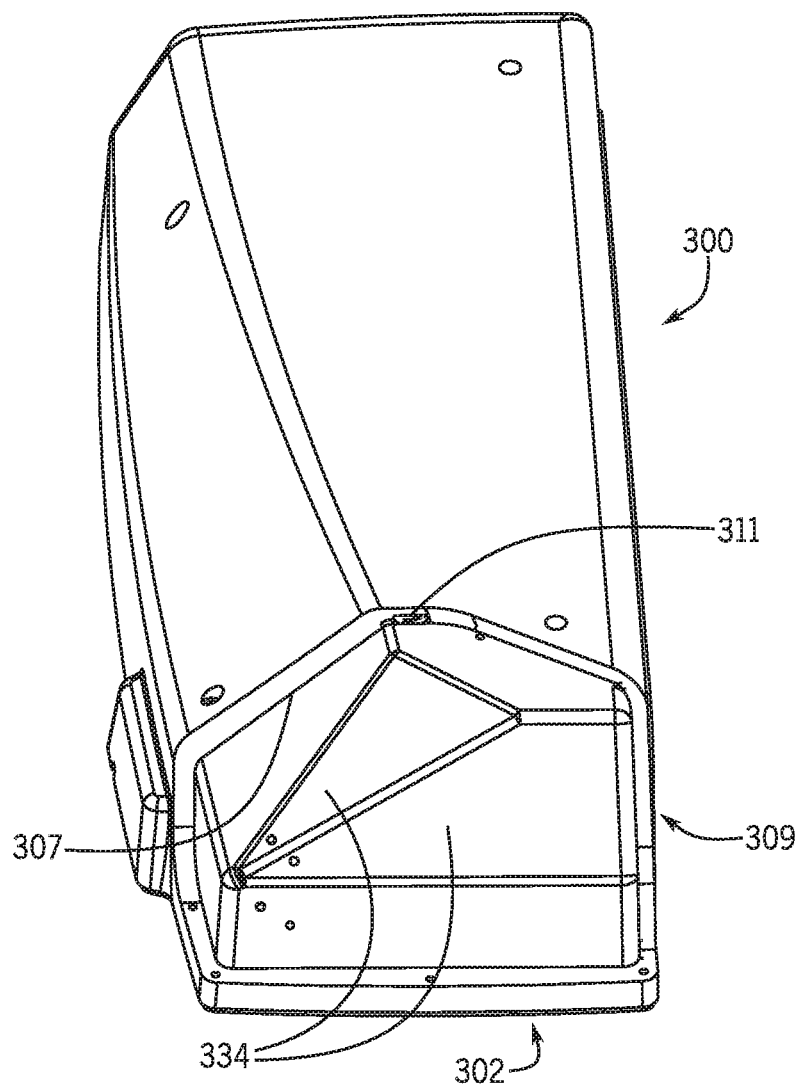
FIG. 10 is a perspective view of a bottom surface and distal end of the bottom portion of the robotic mechanism housing of FIG. 9 in accordance with an embodiment.
Figure 11:
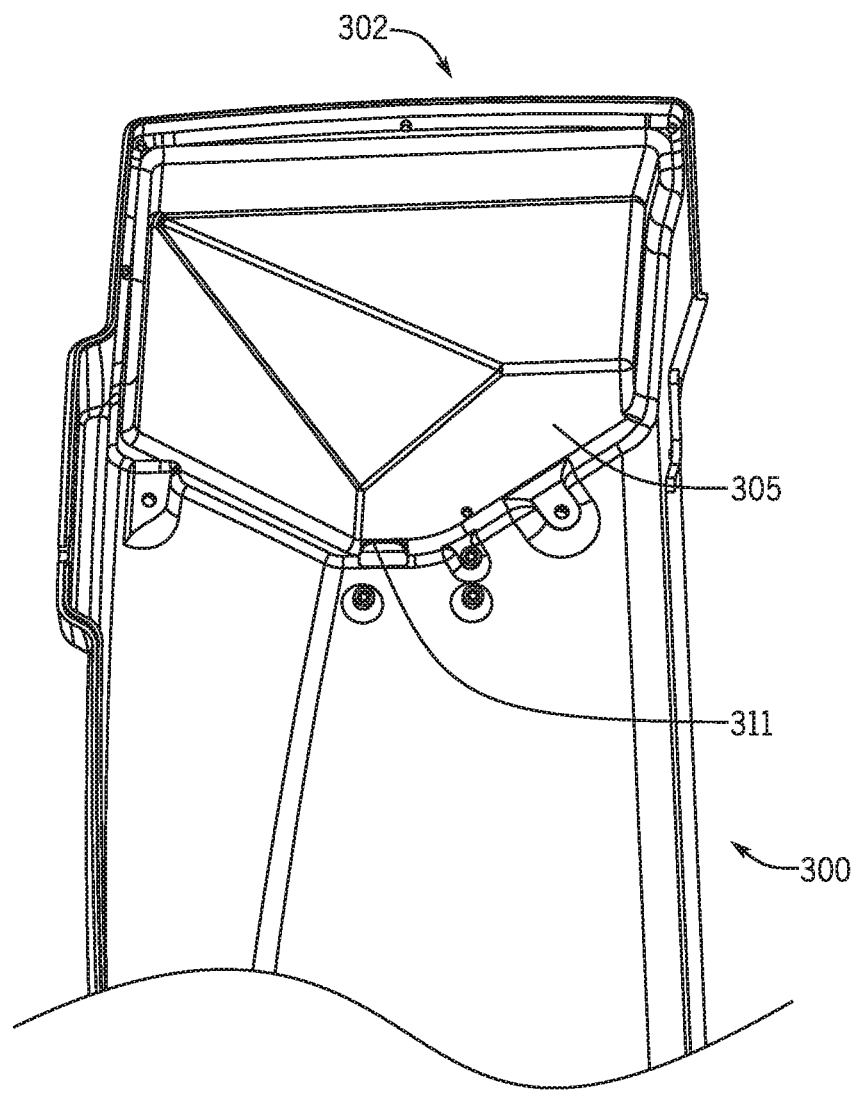
FIG. 11 is a top perspective view of the distal end of the bottom portion of the robotic mechanism of FIG. 9 in accordance with an embodiment.

FIG. 9 is a perspective view of a bottom portion of a robotic mechanism housing in accordance with an embodiment. For example, bottom portion 300 may be part of the housing 282 of the robotic drive base 220 of robotic drive mechanism 212 (shown in FIG. 8). The bottom portion 300 of the housing includes a contact sensor assembly 304 positioned on a distal end 302 of the bottom portion 300 of the housing. FIG. 10 is a perspective view of a bottom surface and distal end of the bottom portion of the robotic mechanism housing of FIG. 9 and FIG. 11 is a top perspective view of the distal end of the bottom portion of the robotic mechanism housing of FIG. 9 in accordance with an embodiment. FIG. 10 shows the bottom portion of the housing in an upside-down position. Referring to FIGS. 9-11, the distal end 302 has an interior surface 305 and an exterior surface 309. The exterior surface 309 of the distal end 302 includes a recess 307 and a plurality of flat sections 334. An aperture 311 in the distal end 302 is used to receive a connector 326 of the contact sensor assembly 304 as discussed further below.

Figure 12:
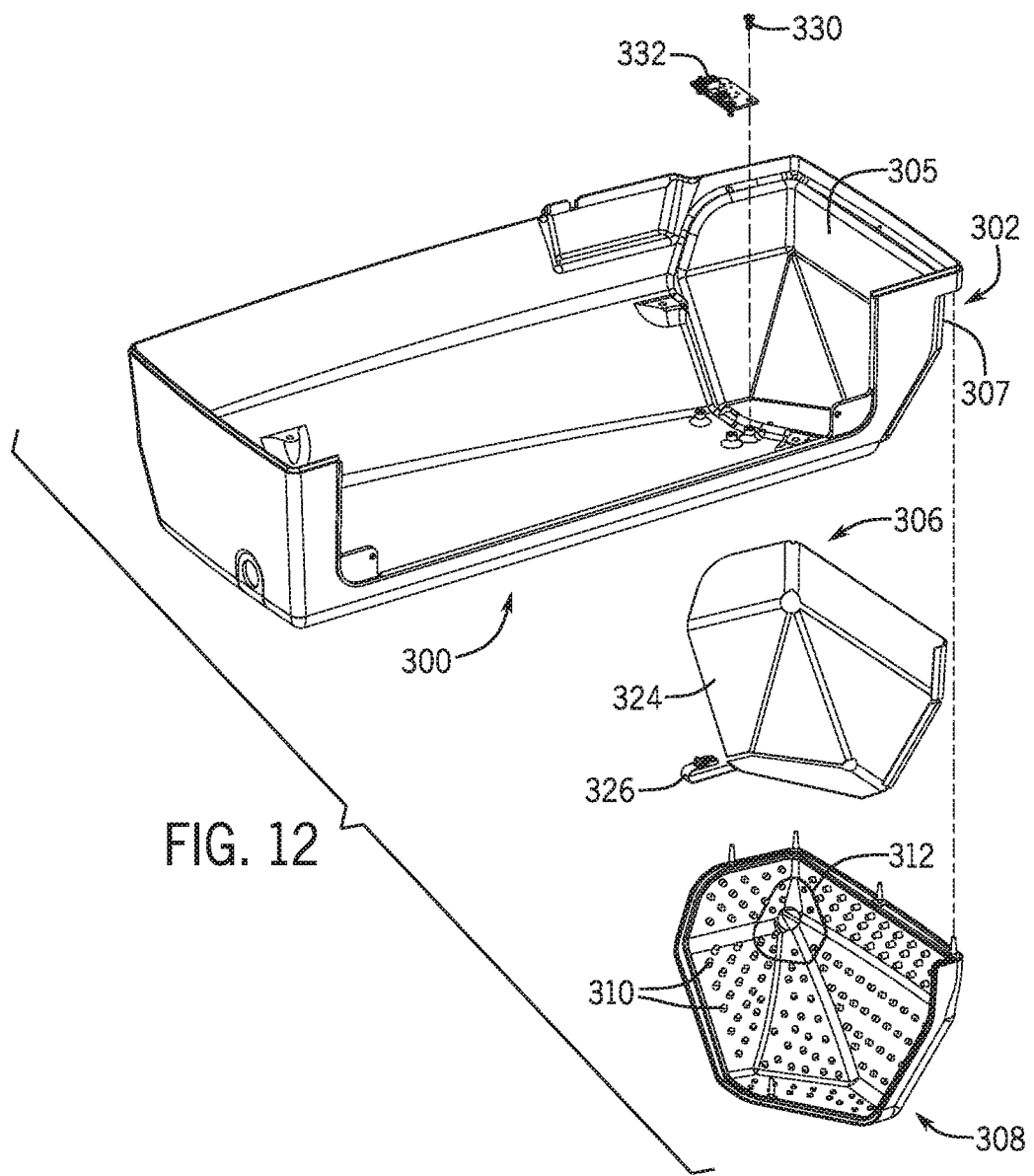
FIG. 12 is an exploded view of a contact sensor assembly in a bottom portion of the robotic mechanism housing in accordance with an embodiment.
Figure 13:
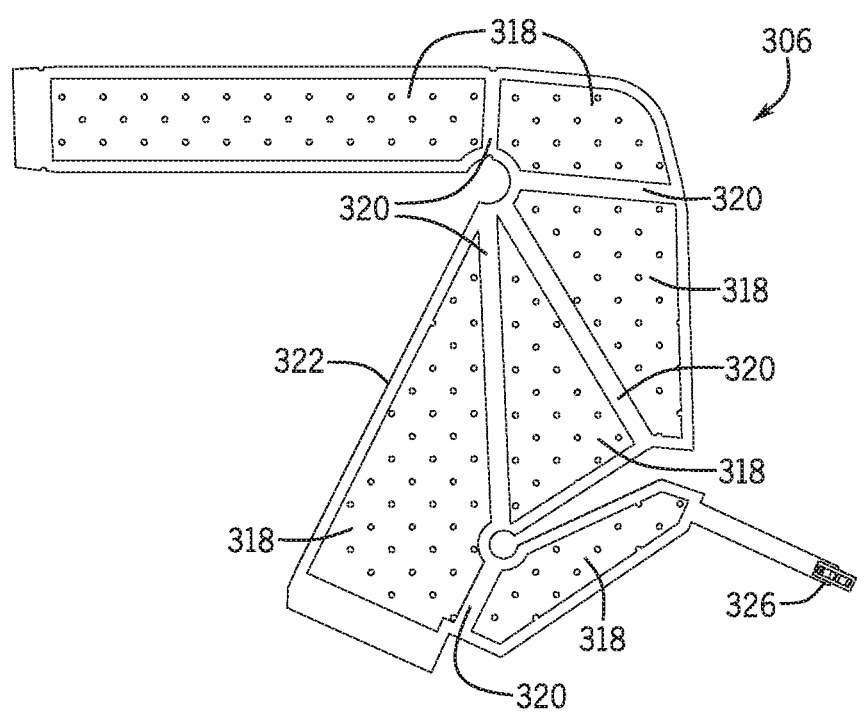
FIG. 13 is a view of a contact sensor in an unassembled flat state in accordance with an embodiment.

FIG. 12 is an exploded view of a contact sensor assembly in a bottom portion of the robotic mechanism housing of FIG. 9 in accordance with an embodiment. The contact sensor assembly includes a contact sensor (or sensor) 306 and an outer cover (or bumper) 308. The sensor 306 and the outer cover 308 are positioned in the recess 307 on the distal end 302 of the bottom portion 300 of the housing. The sensor 306 will now be discussed with reference to FIGS. 12-16. In FIG. 13, an unassembled contact sensor 306 is shown. An outer surface 322 of the sensor 306 includes a plurality of sensing areas 318 and non-sensing areas 320. In a preferred embodiment, each sensing area 318 is configured as a force sense resistor (FSR). In one embodiment, the sensing areas 318 include two interleaved conductive combs (e.g., silver traces) that are not in contact with each other. A connector 326 includes terminals that connect to the sensing areas 318. In one embodiment, the connector has two terminals and each terminal connects to one of the interleaved conductive combs. In other embodiments, other known contact sensing methods may be used to create a force sense resistor.

Figure 14:
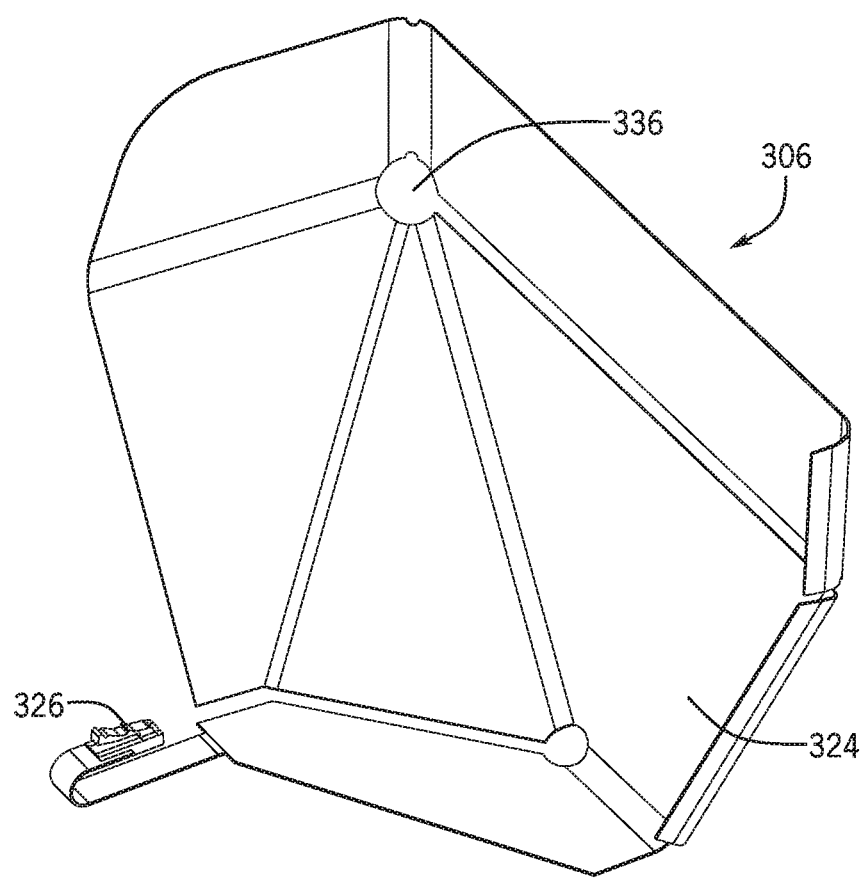
FIG. 14 is a perspective view of the interior side of the assembled contact sensor in accordance with an embodiment.
Figure 15:
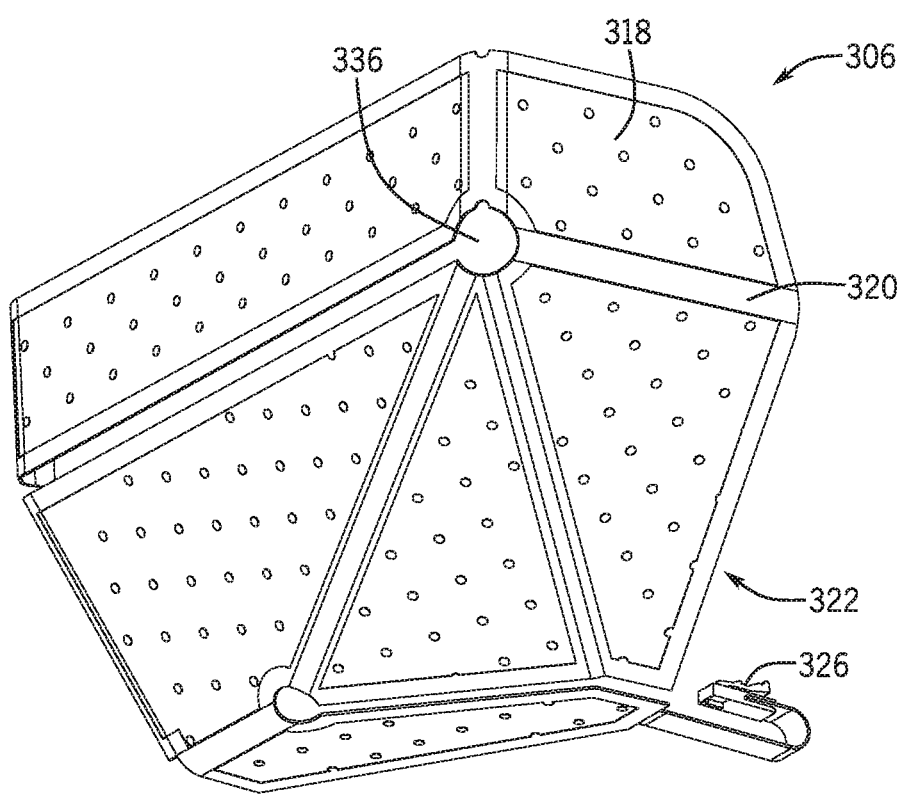
FIG. 15 is a perspective view of the exterior side of the assembled contact sensor in accordance with an embodiment.
Figure 16:
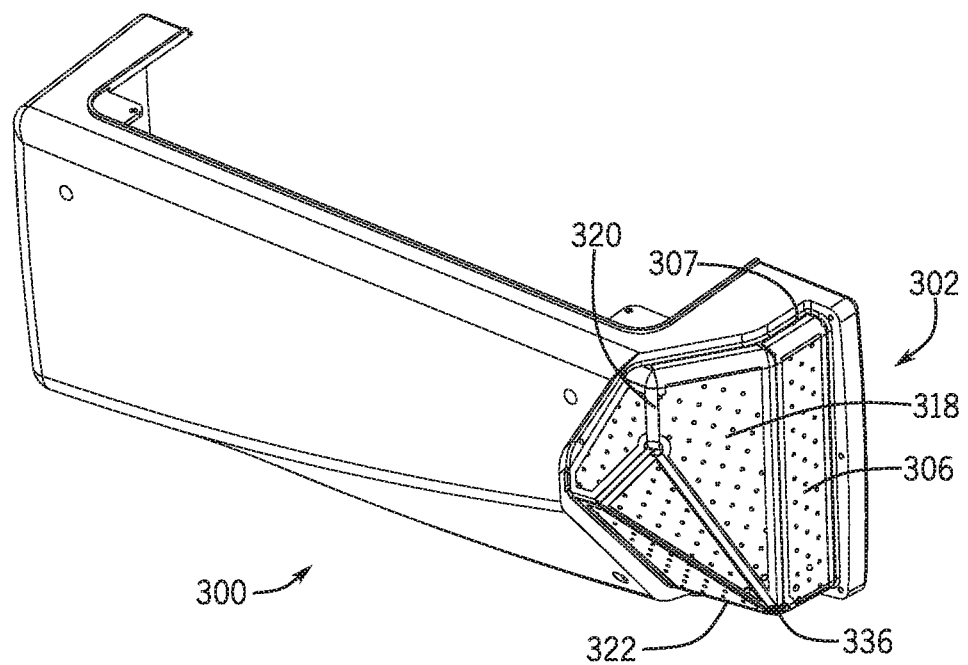
FIG. 16 is a perspective view of the bottom of the contact sensor assembly and housing without the outer cover of the contact sensor assembly in accordance with an embodiment.
Figure 17:
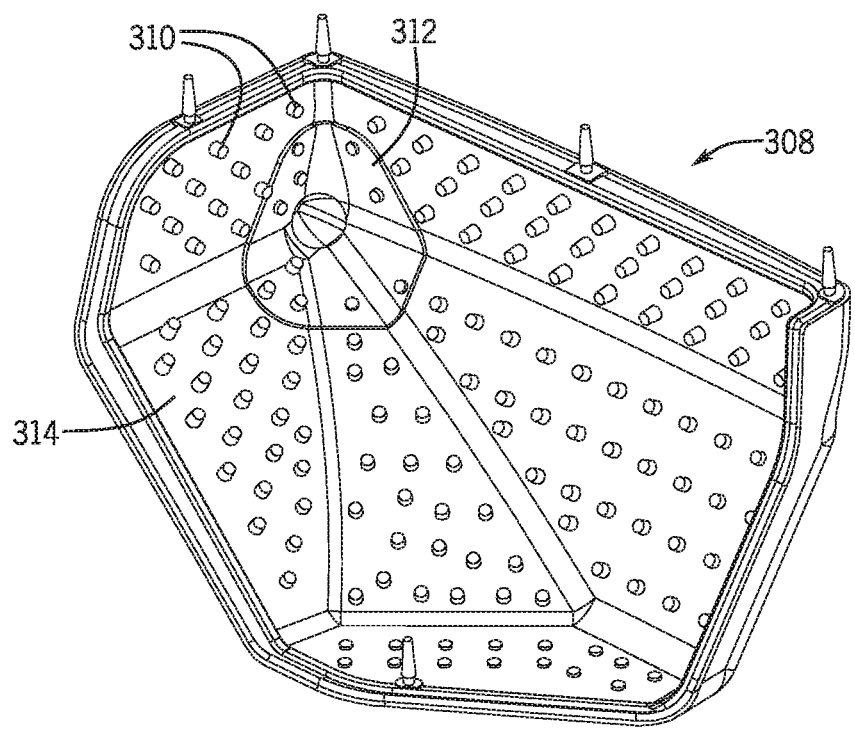
FIG. 17 is a perspective view of the internal surface of an outer cover of the contact sensor assembly in accordance with an embodiment.
Figure 18:
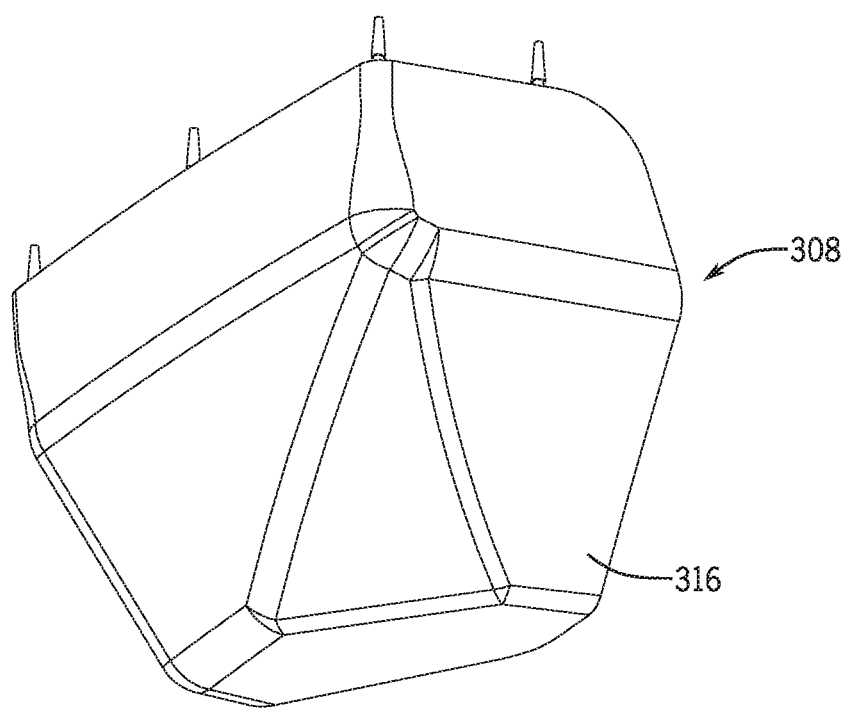
FIG. 18 is a perspective view of an external surface of an outer cover of the contact sensor assembly in accordance with an embodiment.
Figure 19:
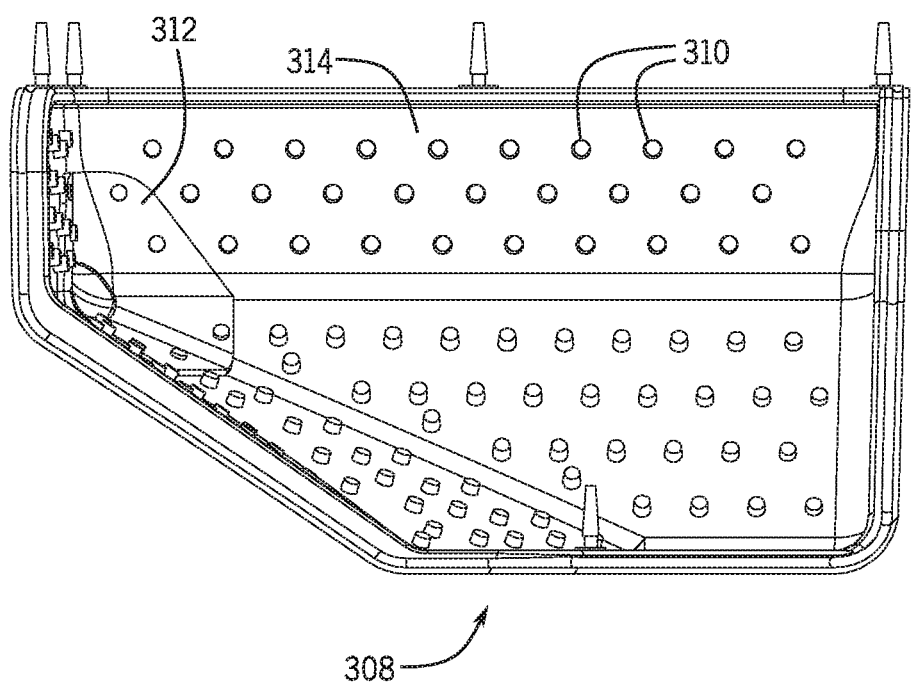
FIG. 19 is an orthographic view of the inner surface of the outer cover of the contact sensor assembly in accordance with an embodiment.

Sensor 306 is configured to be wrapped around and attached to the exterior surface 309 (shown in FIG. 10) of the distal end 302 of the bottom portion 300 of the housing. In an embodiment, each sensing area 318 is applied to a flat section of the exterior surface 309 of the distal end 302 of the bottom portion 300 of the housing. FIG. 15 shows an outer surface 322 of an assembled contact sensor 306. The non-sensing areas 320 of the sensor 306 correspond to where the sensor 306 is bent so that the sensing areas 318 conform to a flat section 334 (shown in FIG. 10) of the distal end 302 of the bottom portion 300 of the housing. FIGS. 12 and 14 show an inner surface 324 of an assembled contact sensor 306. In one embodiment, the inner surface 324 of sensor 306 includes an adhesive to adhere the sensor 306 to the exterior surface 309 of the distal end 302 of the bottom portion 300 of the housing. FIG. 16 shows the distal end 302 of the bottom portion 300 of the housing after the sensor 306 has been attached using, for example, an adhesive. As mentioned, the sensor 306 is wrapped around the exterior surface 309 of the distal end 302 so that the sensing areas 318 are applied and correspond to the flat sections of the exterior surface 309.

Referring to FIGS. 12 and 17-19, the contact sensor assembly also includes an outer cover (or bumper) 308. In one embodiment, outer cover 308 is made of a flexible material such as rubber. The outer cover 308 has an inner surface 314 and an outer surface 316. Outer cover 308 is positioned over the contact sensor 306 and attached to the distal end 302 of the bottom portion 300 of the housing using, for example, an adhesive. In an embodiment, the outer surface 316 of the outer cover 308 is given a similar appearance as the bottom portion 300 of the housing. The inner surface 314 of the outer cover 308 includes a plurality of raised portions 310 (e.g., a boss, pin or stud) which are normally not in contact with the sensor 306. When the outer surface 316 of the outer cover 308 makes contact with an object or obstacle, the raised portions 310 make contact with the outer surface 322 (shown in FIGS. 13 and 16) of the sensor 306. In particular, at least a subset of the raised portions 310 will make contact with at least one sensing area 318 of the sensor 306. Inner surface 314 also includes a corner section 312 that has a greater thickness (e.g., reinforced) than the remainder of the inner surface 314. The reinforced corner section 312 is configured to have a greater stiffness than the remainder of the inner surface 314. The corner section 312 is configured to an area including a corner 336 (shown in FIGS. 14-16) of the sensor 306 where there is not a sensing area. Accordingly, if contact is made at the corner section 312 of the outer cover 308, the reinforced corner section 312 will make contact with at least one of the sensing areas 318 surrounding the corner 336 of the contact sensor 306. In one embodiment, the outer cover 308 is configured so that a predetermined amount of force (or a predetermined force threshold) is required to cause the raised portions 310 or the corner section 312 to make contact with the outer surface 322 of the sensor 306.

Figure 20:
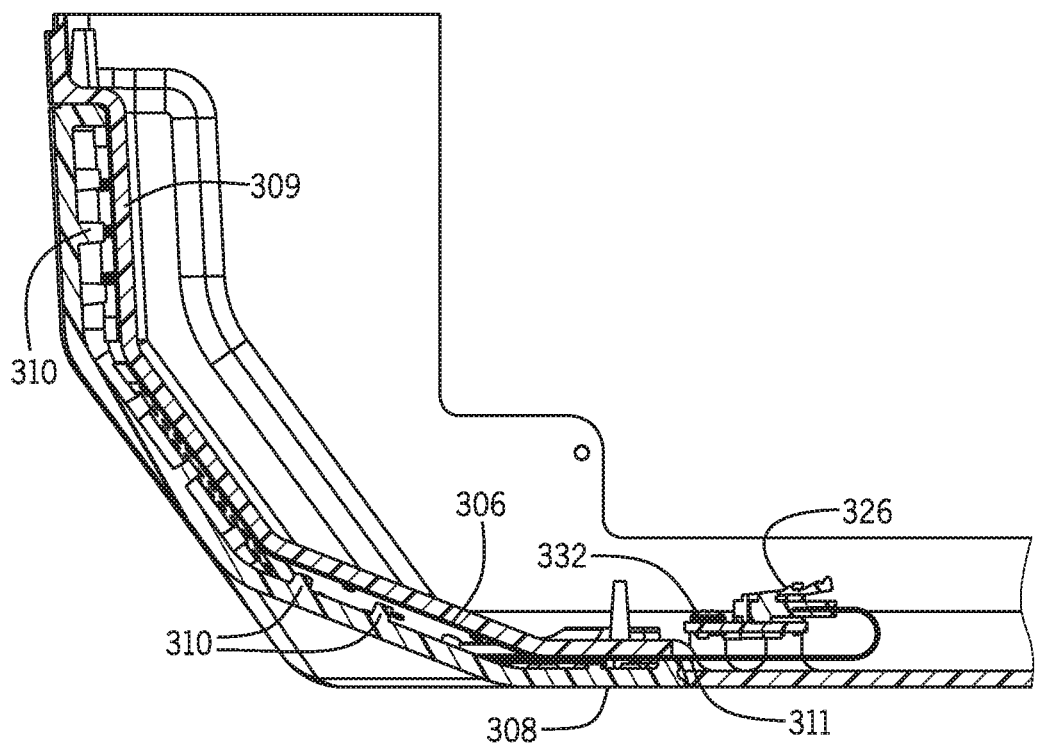
FIG. 20 is a cross-sectional view of the contact sensor assembly in the bottom portion of the robotic mechanism housing in accordance with an embodiment.

Referring to FIGS. 9 and 12, when the sensor 306 is wrapped around the exterior surface 309 (shown in FIG. 10) of the distal end 302, the connector 326 is inserted through the aperture 311 (shown in FIGS. 10, 11 and 20). The connector 326 is coupled to a processor 332 (e.g., a PCB). The processor 322 may be located in the bottom portion 300 of the housing and attached to the bottom portion 300 of the housing using one or more attachment devices 330 such as, for example, a screw. In an embodiment, the processor 332 is also coupled to the controller 134 (shown in FIG. 2) of the catheter procedure system 100. In another embodiment, the processor 332 may be located in the workstation 116 (shown in FIG. 1) and coupled to the connector 326 and the controller 134. FIG. 20 is a cross-sectional view of the contact sensor assembly in the bottom portion of the robotic mechanism housing in accordance with an embodiment. As discussed above, the outer cover 308 of the contact sensor assembly is positioned over the sensor 306 and attached to the bottom portion 300 of the housing. The sensor 306 is attached to the exterior surface 309 of the distal end 302 of the bottom portion 300 of the housing. The connector 326 of the sensor 306 is inserted through the aperture 311 and coupled to the processor 332. When contact is made with the outer cover 308, for example, with a force that exceeds a predetermined threshold, the raised portions 310 on the inner surface of the outer cover 308 or the corner section 312 make contact with the sensor 306, for example, with at least one sensing area 318 (shown in, for example, FIG. 18).

The processor 332 is configured to generate a signal indicating that contact is detected and communicate the signal to the controller 134 (shown in FIG. 2). In one embodiment, the processor 332 is coupled to the two terminals of the connector 326 and monitors the resistance between the two terminals. For example, if there is contact on the outer cover 308 that causes the raised portions 310 or corner section 312 to make contact with at least one sensing area 318 of the sensor 306, the resistance between the two terminals may drop. In one embodiment, if the resistance drops below a predetermined threshold, the processor 332 generates a signal (e.g., a digital signal) indicating there has been contact. The signal is sent to the controller 134 and the controller 134 generates an alert (e.g., visual or audible) for the user via a user interface and/or display. In one example, a symbol may be displayed on the user interface or display. In another example, an error noise may be generated by the controller. In addition, the controller 134 is configured to stop the advancement of the robotic mechanism in response to the signal indicating contact has been detected. Once the object or obstacle is removed, the user may continue the procedure, for example, from the point the procedure/advancement was stopped when contact was detected by the contact sensor assembly. In another embodiment, the processor 332 may be configured to detect whether the contact sensor 306 is operating properly. A resistor (not shown) of a high (but not infinite) fixed resistance may be connected in parallel with the terminals of the connector 326. When contact is made with at least one sensing area 318, the resistance presented to the processor 332 by the terminals will drop (e.g., to a low resistance) and the high resistance of the fixed resistance resistor is short circuited. If there is no contact with any of the sensing areas 318, the resistance presented to the processor 332 will be the known high resistance of the fixed resistance resistor. If the resistance presented to the processor 332 is higher than the known resistance of the fixed resistance resistor, the sensor 306 is considered to be malfunctioning, e.g., not connected properly. The processor may be configured to output a signal (e.g., a forward-enable signal) allowing forward movement of the robotic mechanism only while the high resistance of the fixed resistance resistor alone is detected by the processor 332.

Computer-executable instructions for sensing contact on a robotic mechanism in a catheter procedure system according to the above-described method may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A catheter procedure system comprising:
   a bedside system comprising at least one percutaneous device and at least one drive mechanism coupled to the at least one percutaneous device, the drive mechanism comprising a housing having a distal end and a contact sensor assembly positioned on the distal end of the housing, the contact sensor assembly comprising:
     a sensor comprising a plurality of sensing areas, a plurality of non-sensing areas and a connector coupled to the plurality of sensing areas; and
     an outer cover positioned over the sensor, the outer cover having an inner surface and an outer surface, the inner surface comprising a plurality of raised portions, the raised portions being configured to make contact with the sensor when the outer cover makes contact with an object or obstacle;
   a processor coupled to the contact sensor assembly; and
   a workstation coupled to the bedside system, the workstation comprising:
     a user interface;
     at least one display; and
     a controller coupled to the bedside system, the user interface, the at least one display and the processor coupled to the contact sensor assembly.

2. The catheter procedure system according to claim 1, wherein the outer cover further comprises at least one corner section, the at least one corner section is reinforced so that the corner section has a greater stiffness and the corner section corresponds to at least one non-sensing area of the sensor.

3. The catheter procedure system according to claim 2, wherein the at least one corner section corresponds to a corner of the sensor.

4. The catheter procedure system according to claim 1, wherein the distal end of the housing has a plurality of flat sections and the sensor is configured to be attached to the plurality of flat sections, wherein each sensing area of the plurality of sensing areas corresponds to a flat section and each non-sensing area of the plurality of non-sensing areas corresponds to a location where the sensor is bent so that each sensing area conforms to a flat section of the distal end of the housing.

5. The catheter procedure system according to claim 1, wherein the processor is configured to generate a signal indicating contact with an object and to communicate the signal to the controller.

6. The catheter procedure system according to claim 5, wherein the controller generates an alert on the display based on the signal received from the processor.

7. The catheter procedure system according to claim 1, wherein the processor is configured to generate a signal to allow forward motion of the drive mechanism if no contact with an object is detected and to communicate the signal to the controller.

8. The catheter procedure system according to claim 1, wherein the processor is configured to determine if the sensor is malfunctioning.

* * * * *